(12) United States Patent
Vela et al.

(10) Patent No.: US 12,196,666 B2
(45) Date of Patent: Jan. 14, 2025

(54) SYSTEM AND METHOD FOR DETECTING BIOFILM GROWTH IN WATER SYSTEMS

(71) Applicant: NCH Corporation, Irving, TX (US)

(72) Inventors: David F. Vela, Euless, TX (US); Adrian J. Denvir, Richardson, TX (US); Matthew C. Holloway, Fort Worth, TX (US)

(73) Assignee: NCH Corporation, Irving, TX (US)

( * ) Notice: Subject to any disclaimer, the term of this patent is extended or adjusted under 35 U.S.C. 154(b) by 203 days.

(21) Appl. No.: 17/569,684

(22) Filed: Jan. 6, 2022

(65) Prior Publication Data

US 2022/0128453 A1 Apr. 28, 2022

Related U.S. Application Data

(63) Continuation of application No. 14/681,777, filed on Apr. 8, 2015, now Pat. No. 12,031,901.
(Continued)

(51) Int. Cl.
*G01N 17/00* (2006.01)
*C02F 1/50* (2023.01)
(Continued)

(52) U.S. Cl.
CPC ............ *G01N 17/008* (2013.01); *C02F 1/50* (2013.01); *C12Q 1/06* (2013.01); *C12Q 1/18* (2013.01);
(Continued)

(58) Field of Classification Search
None
See application file for complete search history.

(56) References Cited

U.S. PATENT DOCUMENTS

| 5,185,533 A | 2/1993 | Banks |
| 5,349,874 A | 9/1994 | Schapira et al. |

(Continued)

FOREIGN PATENT DOCUMENTS

| CN | 1154140 | 7/1997 |
| CN | 1420088 | 5/2003 |

(Continued)

OTHER PUBLICATIONS

Simoes, et al., Drinking Water Biofilm Assessment of Total and Culturable Bacteria Under Different Operating Conditions, Biofouling, 2006; 22(2): 91-99.
(Continued)

*Primary Examiner* — Benjamin M Kurtz
(74) *Attorney, Agent, or Firm* — Scheef & Stone, LLP; Robin L. Barnes (57) ABSTRACT

A system and method for monitoring or detecting a level of biofilm growth in a fluid system and controlling operating parameters of the fluid system based a measured level of growth. The monitoring system and method comprises a dye injection system for periodically injecting dye into a portion of fluid from the fluid system, passing the portion of fluid though a narrow lumen tube to achieve laminar flow and using a light source and optical sensor to detect a transmission or emission indicating a level of biofilm growth in the tube corresponding to a level of growth on components in the fluid system. Information based upon the measurements or calculations made by the monitoring system may be used to manually or automatically alter various operating parameters to control the fluid system and aid in maintaining stable operation of the fluid system within preferred specifications.

19 Claims, 10 Drawing Sheets

Related U.S. Application Data (60) Provisional application No. 61/977,464, filed on Apr. 9, 2014.

(51) Int. Cl.

| | | |
|---|---|---|
| *C02F 103/02* | (2006.01) | |
| *C12Q 1/06* | (2006.01) | |
| *C12Q 1/18* | (2006.01) | |
| *G01N 21/01* | (2006.01) | |
| *G01N 21/17* | (2006.01) | |
| *G01N 21/25* | (2006.01) | |
| *G01N 21/27* | (2006.01) | |
| *G01N 21/31* | (2006.01) | |
| *G01N 21/49* | (2006.01) | |
| *G01N 21/53* | (2006.01) | |
| *G01N 21/64* | (2006.01) | |
| *C12M 1/26* | (2006.01) | |
| *F17D 1/08* | (2006.01) | |

(52) U.S. Cl.
CPC ............. *G01N 21/01* (2013.01); *G01N 21/17* (2013.01); *G01N 21/25* (2013.01); *G01N 21/53* (2013.01); *A61M 2206/11* (2013.01); *C02F 2103/023* (2013.01); *C02F 2303/20* (2013.01); *C02F 2307/14* (2013.01); *C12M 1/267* (2013.01); *F17D 1/08* (2013.01); *G01N 21/27* (2013.01); *G01N 2021/3181* (2013.01); *G01N 21/49* (2013.01); *G01N 2021/6439* (2013.01)

(56) References Cited

U.S. PATENT DOCUMENTS

| | | | |
|---|---|---|---|
| 5,541,056 A | 7/1996 | Huntley et al. | |
| 5,716,852 A | 2/1998 | Yager et al. | |
| 5,948,684 A | 9/1999 | Weigl et al. | |
| 5,972,710 A | 10/1999 | Weigl et al. | |
| 6,171,865 B1 | 1/2001 | Weigl et al. | |
| 6,311,546 B1 | 11/2001 | Dickinson | |
| 6,329,165 B1 | 12/2001 | Chattoraj et al. | |
| 6,455,031 B1 | 9/2002 | Davies | |
| 6,582,963 B1 | 6/2003 | Weigl et al. | |
| 6,800,478 B2 | 10/2004 | Castellini | |
| 7,190,457 B2 | 3/2007 | Tabacco et al. | |
| 7,341,841 B2 | 3/2008 | Metzger et al. | |
| 7,452,726 B2 | 11/2008 | Chou et al. | |
| 7,687,239 B2 | 3/2010 | Goldberg et al. | |
| 7,691,333 B2 | 4/2010 | McBride et al. | |
| 7,837,946 B2 | 11/2010 | McBride et al. | |
| 7,883,622 B1 | 2/2011 | Barnes | |
| 7,905,245 B2 | 3/2011 | McQuade et al. | |
| 8,007,746 B2 | 8/2011 | Unger et al. | |
| 8,071,319 B2 | 12/2011 | Metzger et al. | |
| 8,343,442 B2 | 1/2013 | McBride et al. | |
| 8,460,887 B2 | 6/2013 | Goldberg et al. | |
| 8,481,302 B2 | 7/2013 | Boyette | |
| 8,658,418 B2 | 2/2014 | Daridon | |
| 2002/0037260 A1 | 3/2002 | Budney et al. | |
| 2002/0068312 A1 | 6/2002 | Castellini | |
| 2003/0012688 A1 | 1/2003 | Kippenhan | |
| 2006/0257969 A1 | 11/2006 | Hug | |
| 2008/0076147 A1 | 3/2008 | Ei-Azizi | |
| 2008/0318269 A1 | 12/2008 | Olson et al. | |
| 2009/0214674 A1 | 6/2009 | Barraud | |
| 2009/0218527 A1 | 9/2009 | French | |
| 2011/0216953 A1 | 9/2011 | Callahan | |
| 2011/0319808 A1 | 12/2011 | Bowler | |
| 2012/0122729 A1 | 5/2012 | Musken et al. | |
| 2012/0245506 A1 | 9/2012 | Piergallini | |
| 2013/0161265 A1 | 6/2013 | Fox et al. | |
| 2013/0161268 A1 | 6/2013 | Fox et al. | |
| 2013/0344533 A1 | 12/2013 | Kotzer et al. | |
| 2015/0191765 A1 | 7/2015 | Bassler et al. | |

FOREIGN PATENT DOCUMENTS

| | | |
|---|---|---|
| WO | WO2001049876 | 7/2001 |
| WO | WO2013134180 | 9/2013 |

OTHER PUBLICATIONS

Funfak et al., "Synergistic effects of metal nanoparticles and a phenolic uncoupler using microdroplet-based two-dimensional approach", Journal of Environmental Monitoring, 2011, vol. 13, No. 2, p. 410-415.

Rusconi et al. (J.R. Soc. Interface, 2010, 7, 1293-1299)(Year: 2010).

Leica SP5 System Specification, p. 1, accessed online Apr. 29, 2019. (Year: 2019).

Olympus ("Introduction to Confocal Microscopy", pp. 1-8, accessed online Oct. 23, 2018) (Year: 2018).

O'Toole et al. (Molecular Microbiology, 1998, 30, 295-304) (Year: 1998).

Blachere, H. and Jamart, G., A Flow Cell photometer for Bacterial Growth Monitoring, Biotechnology and Bioengineering, vol. XI, Jan. 1, 1969, pp. 1005-1010.

Fellers, et al., Introduction to Confocal Microscopy, Microscopy Resource Center, Olympus America, Inc., pp. 1-8, accessed online Oct. 23, 2018.

Reggiani et al: "Trasar Technology—A Review and Comparison Cooling Water Feed Control Automation Basic Trasar Concept Introduction to Fluorescence", Sep. 22, 2004. Retrieved from the Internet: URL: http://go2eti.com/downloads/AWT_Trasar Paper_Final.pdf retrieved on Aug. 3, 2017.

Olympus FV 1000 (pp. 1-28, accessed online Sep. 11, 2020 at https://www.olympusamerica.com/files/seg_bio/fv1000_brochure.pdf, which cites a 2004 study that uses the disclosed model—see bottom of p. 14) (Year 2004).

Pullia et al. (Review of Scientific Instruments, 2012, 83, 104704) (Year 2012).

SYSTEM AND METHOD FOR DETECTING BIOFILM GROWTH IN WATER SYSTEMS

CROSS REFERENCE TO RELATED APPLICATION

This application is a continuation of U.S. application Ser. No. 14/681,777 filed Apr. 8, 2015, which claims the benefit of U.S. Provisional Application Ser. No. 61/977,464 filed on Apr. 9, 2014.

BACKGROUND OF THE INVENTION

1. Field of the Invention

This invention relates to detecting and monitoring biofilm formation within anthropogenic water and other fluid systems to provide information to aid in controlling the operation and treatment of the water or other fluid system.

2. Description of Related Art

Many anthropogenic water or fluid systems, such as cooling towers and boilers, are prone to growth of biofilms. Biofilms contain mixed communities of bacteria that adhere to surfaces, such as pipe walls, of components within the fluid system. The bacteria in underlying layers of biofilms continue to reproduce and create a dense bacterial cluster. As these biofilm layers form they also accumulate other inorganic and organic debris, increasing in size and restricting flow with the fluid system and causing blockages, which can result in increasing operating costs (such as pumping requirements) and maintenance costs for the fluid system. Various chemical treatments and biocides are known to be added to such fluid systems to remove biofilms and aid in controlling growth and recolonization. Effective treatment to remove biofilms and to prolong the amount of time before the fluid systems are re-contaminated can save significant amounts of money. An effective and thorough treatment may save costs for labor and treatment chemicals by reducing the frequency of periodic treatments or reducing the amount of chemicals needed for routine maintenance and/or periodic treatments. Such a treatment may also save on energy costs through the operation of clean heat exchange surfaces and reduce the amount of bleed-off/make-up cycles to remove contaminated water and replace it with fresh water.

In order to effectively control and treat biofilms in fluid systems, it is beneficial to be able to monitor the growth of biofilms within the fluid system. Some fluid systems are on a periodic treatment schedule without any means of detecting biofilms, which results in treating the fluid system when not needed. This can be costly and can result in unnecessary damage to components of the fluid system since many biofilm treatments are acidic or corrosive. Some fluid systems rely on visual inspection of components to determine the presence of biofilm growth. This can make it difficult to detect the presence of biofilms in areas of the fluid system that are not easily inspected by visual means.

It is also known to use an automated monitoring system to monitor for biofilm growth or other types of contaminants in a fluid system. For example, US Patent Application Publication No. 2013/0344533 discloses a "scaffold" structure biosensor with an embedded dye/clay mixture. A portion of water is withdrawn from the fluid system and enters a "dampening basin" upstream of the biosensor to achieve laminar flow over a scaffold structure biosensor. If microorganisms are present, there is a reaction with the dye embedded in the scaffold and a signal detection unit may be used to detect a change in color. The disadvantages of such a monitoring system include that preparation of the dye/clay mixture embedded in the sensor scaffold is difficult and requires replacement of the entire biosensor structure when replenishment is needed. Additionally, it appears that the flow of sample water is continuously exposed to the dye/clay mixture, which would cause the dye to be consumed more quickly and increases maintenance time and costs. Finally, it appears that the sample water is in an open biosensor structure where it could be contaminated by external contaminants.

Another automated monitoring system and method is disclosed in U.S. Pat. No. 7,190,457. The system described in the '457 patent uses multiple optical probes to obtain signals indicating biofilm growth and can differentiate between bulk or suspended bacteria and biofilm growth. The system in the '457 patent can be used externally to the fluid system, with an isolated sample of fluid disposed on a representative substrate, such as glass or metal, or it can be used by directly inserting the optical probed into the flow of fluid within the fluid system. The disadvantage of the external configuration is that it requires removal of samples from the fluid system and is not as accurate as a measurement of fluid flowing through the fluid system. The disadvantages of the direct application are that it requires waterproof components and does not take advantage of any laminar flow characteristics in the area where the test is being conducted.

None of the known prior art references disclose a closed biofilm monitoring or detecting system for use in-line with a flowing fluid system that uses a dye that is injectable at the time of or near the time of measuring or detecting biofilm growth, that does not require waterproof light source or optical detector components, and that incorporates laminar flow characteristics in the area to be tested. There is a need for a simple monitoring system that can be easily added on to existing fluid systems and that is capable of automated, in-line monitoring for biofilm growth and automated control of operational parameters of the fluid system in response to detected biofilm growth.

SUMMARY OF THE INVENTION

This invention provides a system and method for real-time detection and monitoring of biofilm formation within anthropogenic water and other fluid systems, such as a cooling tower or boiler system, to provide information to aid in controlling the operation and treatment of the water or other fluid system. A monitoring or detecting system according to a preferred embodiment of the invention comprises a narrow lumen tube through which a portion of water or fluid from the fluid system is diverted and flows and into which an amount of bio-reactive dye is periodically injected. The narrow lumen tube passes through a sensor comprising a light source and optical detector that periodically measures a light transmission or emission corresponding to growth of a biofilm within the tube. The use of a narrow lumen tube allows for laminar flow through the test or measurement area at the sensor, which is characterized by the flow rate of water or other fluid being at its maximum velocity through the center of the lumen and being virtually zero at the lumen walls (the hydrodynamic boundary layer). The physics of laminar flow allow microbial adhesion and subsequent biofilm formation on the inner walls of the narrow lumen tube, resulting in biofilm growth in the monitoring or detecting system that corresponds to biofilm growth or favorable biofilm growth conditions within the fluid system. The biofilm growth in the narrow lumen tube would grow faster than expected in most parts of the fluid system. Depending on the level of growth of biofilm in the narrow lumen tubing, the monitoring and detecting system may indicate when conditions in the fluid system favor biofilm growth or may indicate that biofilm growth is already occurring in the fluid system. Thus the monitoring and detecting system can provide early warning or indication of a potential biofilm issue in the fluid system or the likely existence of actual biofilm in the fluid system.

According to another preferred embodiment of the invention, a bio-reactive dye is periodically injected into the narrow lumen tube through which the fluid to be tested flows. A preferred dye is Erythrosine, which selectively binds to bacterial cells. Dye is only injected at or near the time a measurement is made using a light source and optical detector that detects a transmission or emission of light through the tube or from the dye within the tube. This configuration conserves the amount of dye used in the system. According to another preferred embodiment, the monitoring system comprises a dye reservoir for containing the dye to be injected, a control valve that periodically opens and closes to release an amount of dye from the reservoir, and a venturi injector that injects the released dye into a tube through which the fluid to be tested is flowing.

According to another preferred embodiment of the monitoring system, the fluid to be tested flows through the monitoring system, the level of biofilm growth is measured, and the fluid is returned to the fluid system. During normal operations of the fluid system and monitoring system, fluid continuously is withdrawn from the fluid system, flows through the monitoring system and is returned to the fluid system. The fluid is only measured for detection of biofilm growth at certain intervals, which may be at predetermined and preprogrammed time intervals, when a measurement or the difference between two measurements is above a predetermined threshold, and/or when a manual entry is made to initiate a measurement. Continuously flowing fluid through the monitoring system simulates the flow of fluid through the fluid system, giving the same amount of time for growth of biofilms in the monitoring system as in the fluid system to achieve more accurate measurements corresponding to the level of growth on components in the fluid system.

According to another preferred embodiment of the invention, the monitoring system comprises a plurality of interchangeable, narrow lumen tubing segments. Preferably, these tubing segments would be in a pre-cut format with quick connects for easy install and replacement. According to another preferred embodiment, the monitoring system comprises a housing having inlet and outlet bulkhead fittings that are connectable to tubing or piping in the fluid system to allow a portion of fluid from the fluid system to flow through the monitoring system and then be returned to the fluid system. The narrow lumen tubing segments and inlet and outlet bulkhead fittings preferably have quick connect features allow easy connection of the components to allow fluid to flow from the fluid system, through the monitoring system for measurement and then back to the fluid system, making installation and replacement of tubing easy.

According to another preferred embodiment, a monitoring system is configured to detect the transmission or emission of light from one or more light sources through the fluid flowing in the narrow lumen tube or from a compound or dye injected into the fluid in the narrow lumen tube using one or more optical detectors. A light source and an optical sensor are configured relative to the narrow lumen tube to measure the transmission or emission of light through or from the fluid in the tube. Data or signals from the optical sensor or sensors indicate a level of biofilm growth within the narrow lumen tubing that corresponds to a level of biofilm growth in various parts of the fluid system.

According to yet another preferred embodiment, a monitoring system comprises an display and user interface that provides information regarding the measured or calculated level of biofilm growth and allows a user to input data and instructions into the monitoring system and/or any control system for the fluid system that is connected (by wired or wireless connection) to the monitoring system, such as instructions to run a high resolution test or instructions to add treatment products to the fluid system.

According to another preferred embodiment, a monitoring system comprises a controller with processing capabilities that allow it to send and receive signals, make calculations, display data, store data and/or save data to a removable memory card or other connected device, and process one or more tests that are selected by a user (such as a low resolution or high resolution test). A preferred controller is configured to interact with a light source, optical sensor, dye injector system, and a display and user interface. According to another preferred embodiment, a controller is also capable of automatically sending signals to alter one or more operating parameters of the fluid system, making recommendations for altering operating parameters, and accepting manual input of operating parameter changes and sending signals to other devices or equipment to carry out the manually input changes, in order to control operation of the fluid system. The information provided by the monitoring system may be displayed on a screen on the monitoring system housing, thereby allowing the user to make manual changes to the fluid system based on the information, such as manually adjusting a valve, to manually input instructions into the sensing system meter which are then sent to other devices or equipment or to manually input instructions into a separate electronic control system to make changes to the fluid system based on the information. The information may also be communicated to a separate or remote control system, directly (through a plug-in connection) or by wireless communication, to remote users (such as supervisors or remote operators), to achieve automated control over the fluid system. The monitoring system is preferably part of a larger control system with numerous configurations of applied electronics and the ability to communicate data from the monitoring system to computers or other instruments in order to control operation of a fluid system. The operating parameters (such as rate or amount of treatment product(s) added, "fresh" water or fluid added, blowdown, feed or other fluid system adjustments) may be altered (such as by opening or closing valves in the fluid system, operating pumps, or through manual addition of treatment products or chemicals) would be altered if the information indicates a change is needed, such as when the calculated value of biofilm growth falls outside a specified range or is above or below a pre-set threshold value. Additionally, calculated values may be compared and the difference may indicate a need to alter or automatically trigger an alteration in operating parameters for the fluid system, which may improve accuracy in controlling the fluid system.

According to another preferred embodiment, an alarm signal, such as an audible signal, a visual signal or both, may be generated when a calculated property or value is outside a given range or below or greater than a pre-set value. The alarm signal may be generated by monitoring system and may be communicated wirelessly to a remote control system for the fluid system, computer screen, or user's/supervisor's cell phone or email. According to yet another preferred embodiment, additional alarm signals may also be generated when a calculated level of biofilm growth is within one or more ranges or above or below one or more pre-set values for that property. These additional alarm signals may alert a user when a biofilm level is approaching a value that would require a change in an operating parameter (such as an increase or decrease in treatment product or biocide added to the fluid system) or when the value is at a critical level requiring immediate attention. Preferably, the additional alarm signals are audibly or visually distinct from each other.

BRIEF DESCRIPTION OF THE DRAWINGS

The system and method of the invention are further described and explained in relation to the following drawing wherein.

DESCRIPTION OF THE PREFERRED EMBODIMENTS

Figure 1:
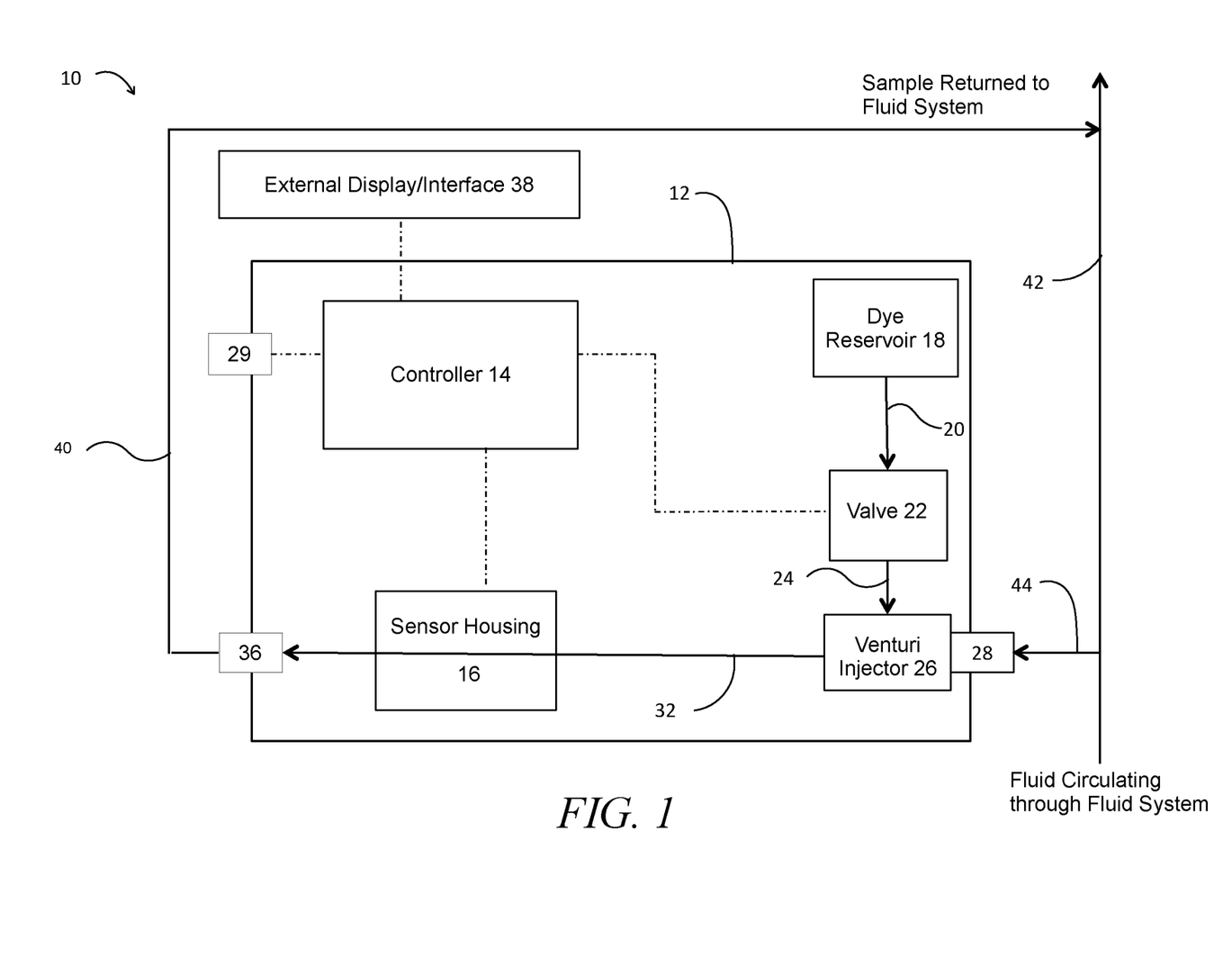
FIG. 1 is block diagram showing a system for detecting biofilm growth according to a preferred embodiment of the invention.

Referring to FIG. 1, a preferred embodiment of a biofilm detecting or monitoring system 10 is depicted in simple, block diagram form. Biofilm detecting or monitoring system 10 preferably comprises a housing 12, a controller 14, a sensor housing 16, a dye reservoir 18, a valve 22, a venturi 26, an inlet port 28, an outlet port 36, and optionally a USB or other type of port 29 for transmission of data received by the controller 14 from a sensor within sensor housing 16. Monitoring system 10 also preferably comprises a plurality of tubing or conduit segments, such as 20, 24, and 32 connecting various components as further described below.

Housing 12 is preferably a waterproof or water-resistant box having a removable cover or openable door allowing access to the interior of housing 12, such as for maintenance or replenishment of the dye in dye reservoir 18. The controller 14, sensor housing 16, dye reservoir 18, valve 22, and venturi 26 are all preferably disposed within housing 12 so they are protected from exposure to water or other fluid from the fluid system or other environmental impacts. Housing 12 also preferably has mounting structure that allows the monitoring system 10 to be mounted or otherwise securely attached to an existing structure (such as a wall) around the fluid system to be tested, preferably near the point where a portion of fluid is withdrawn from the fluid system and diverted to the monitoring system 10.

Figure 8:
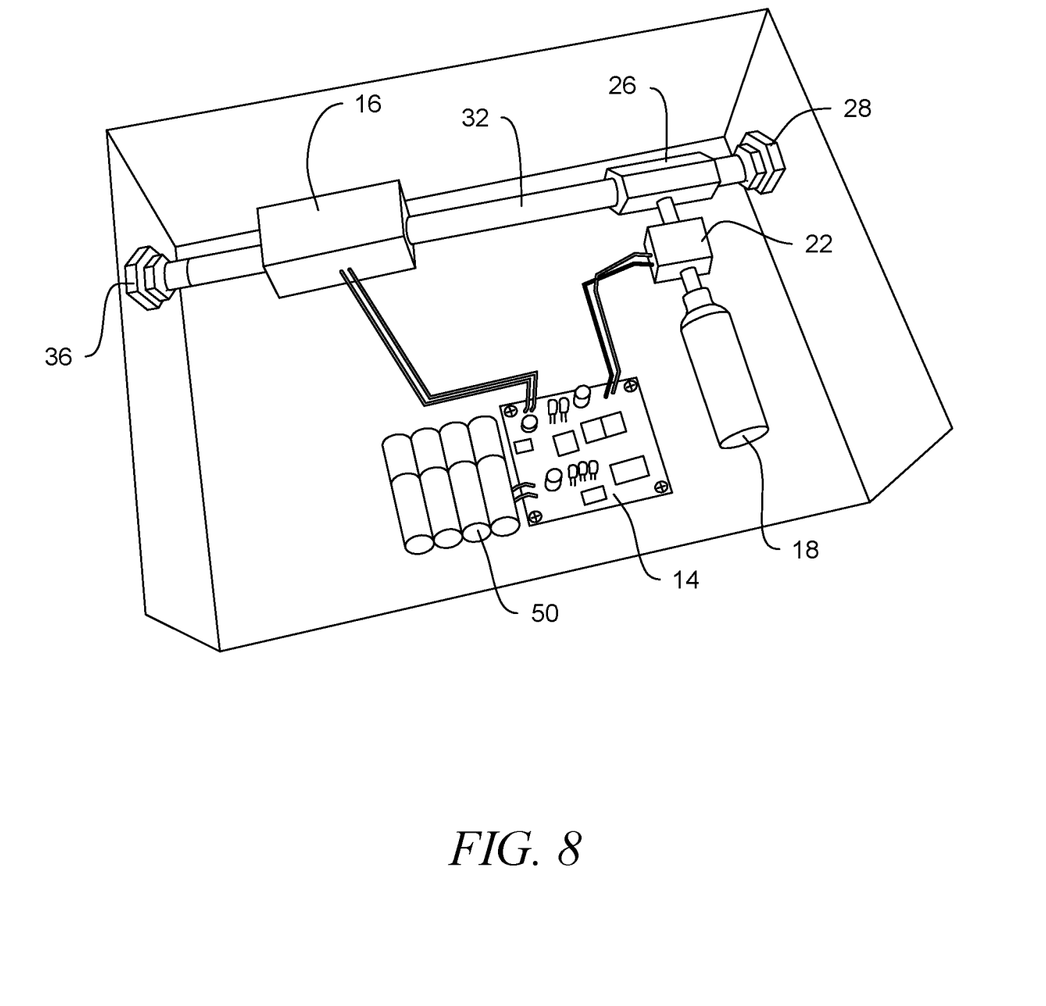
FIG. 8 is a schematic of a system for detecting biofilm growth according to another preferred embodiment of the invention using a batter pack to provide power to a controller.
Figure 9:
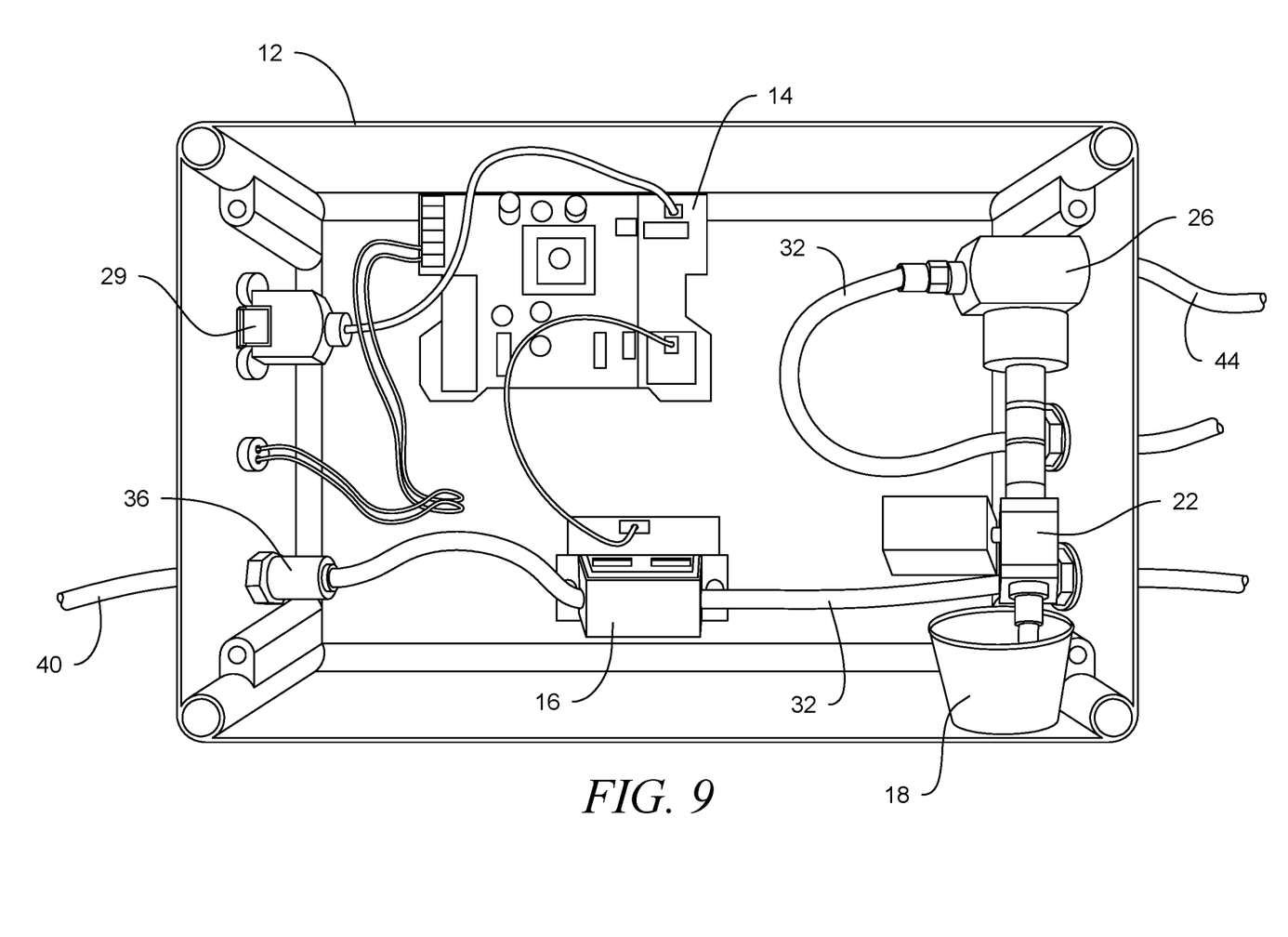
FIG. 9 is a schematic of an as-built prototype system for detecting biofilm growth according to another preferred embodiment of the invention.
Figure 10:
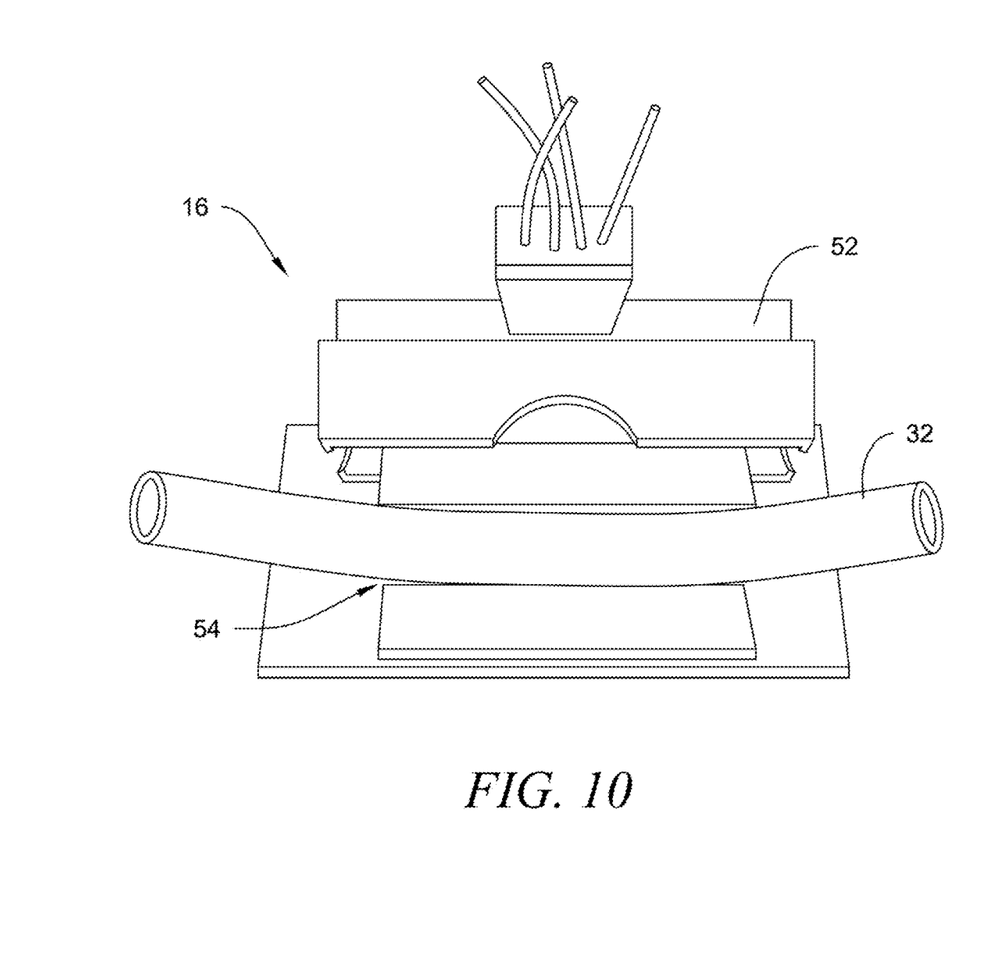
FIG. 10 is a schematic of the sensor housing from the system of FIG. 9 shown in an opened position.

A portion of the fluid flow through the fluid system may be withdrawn from a side stream fluid source (such a coupon rack for example) or from a main line of circulation or fluid flow through the fluid system, depicted in FIG. 1 as line 42, and diverted to the monitoring system 10 through tubing (or piping) 44. Tubing 44 is connected in fluid communication with inlet port or inlet bulkhead fitting 28, which is also directly connected to venturi injector 26. Alternatively, venturi injector 26 could be connected to inlet port 28 by a length of tubing. On a downstream side of venturi injector 26 is tube or tubing 32, which is preferably a narrow lumen tube having a high internal surface area to volume ratio and configured such that, at a constant flow rate through the tubing 32, the velocity of the moving fluid varies from virtually zero at the lumen walls (the hydrodynamic boundary layer) to a maximum flow rate along the center line of tube 32. Most preferably the internal diameter of tube 32 is between about 1 mm to about 20 mm, but other sizes may also be used. Tube 32 passes through sensor housing 16 and is connected on a downstream side of sensor housing 16 to outlet port or outlet bulkhead fitting 36. Preferably, sensor housing 16 is openable to allow for easy insertion of tube 32, as shown in FIG. 10, and then closed around the measurement area of the tube during use. The sensor housing is preferably substantially rectangular in shape with two dimensions (preferably width and height) each sized around 2 to 3 times an external diameter of the measurement area of the tube, as shown in FIGS. 8-10. Most preferably, sensor housing 16 is made from substantially solid, dark colored material to block external light from interfering with the light measurement by the optical sensor once the tube is inserted in the sensor housing 16 and the housing 16 is closed around the measurement area of the tube. Tubing 40 is connected in fluid communication with outlet port 36 to return the fluid from monitoring system 10 back to line 42 of the fluid system. Inlet port 28 and outlet port 36 and venturi injector 26 preferably are threaded or have quick-connecting fittings allowing tubing to be quickly and easily connected or disconnected. Although it is preferred to return the fluid tested in monitoring system 10 to the same source or line 42 from which the fluid was withdrawn, tubing 40 may be connected to any part of the fluid system (preferably downstream from where the fluid was withdrawn for monitoring) to return the fluid to the fluid system. In this way, a portion of fluid from the fluid system continuously flows through monitoring system 10 during normal operations of monitoring system 10 and the fluid system. Valves or other control mechanisms may be added to tubing 44, tubing 40, inlet port 28 and/or outlet port 36 to restrict or stop flow of fluid to monitoring system 10, without necessarily restricting fluid flow through the fluid system, if desired.

A dye reservoir 18 is also preferably disposed inside housing 12. Dye reservoir 18 preferably contains a bio-revealing dye that indicates the presence of biological material when exposed to light within sensor housing 16. The most preferred dye is Erythrosine, but other dyes, such as dental plaque disclosing solution, FDC green number 3, FDC blue number 1, other food dyes and fluorescent dyes or a combination of the foregoing may also be used. A valve 22 is preferably used to control the release of dye from dye reservoir 18 and the dye is injected into the fluid through a venturi injector 26. Valve 22 is preferably a solenoid valve, but other types of valves may also be used. Dye reservoir 18 is preferably connected in fluid communication with tubing 20, which is connected to valve 22 and tubing 24 is connected to venturi injector 26.

A portion of fluid from fluid system to be tested is diverted to monitoring system 10 through tubing 44, as previously described. Dye from dye reservoir 18 is periodically injected into the fluid to be tested and then passes through sensor housing 16 in tubing 32. Sensor housing 16 is preferably a waterproof or water-resistant box having a removable or openable cover or door allowing access to the interior of sensor housing 16, such as for maintenance or replacement of tubing 32, as shown in FIG. 10. Disposed within sensor housing 16 is a light source and an optical sensor or detector, with tubing 32 disposed between the light source and optical sensor in a configuration that allows for detection of optical properties, such as fluorescence of the Erythrosine dye. As shown in FIGS. 8-10, sensor housing 16 is preferably small in size as shown by the relative size of sensor housing 16 to (1) four standard batteries in battery pack 50 (FIG. 8), (2) a connector end of a USB cable inserted into USB port 29 (FIG. 9), and (3) the narrow lumen tubing 32 inserted through sensor housing 16 (FIGS. 9 and 10), which preferably has an internal diameter of 1-20 mm. FIG. 9 is drawn showing the parts to relative scale of an as-built prototype for a preferred embodiment of the invention. A light source within sensor housing 16 is preferably an LED emitting light in a wavelength range of 545 to 570 nm. Detection is accomplished using an ambient light sensor (photo transistor), which allows for current to flow through in proportion to the amount of light hitting the base, this current flows through a resistive network to a corresponding output voltage base. The output data (or signal) from the light sensor (or optical sensor) will be processed by controller 14, which will read real time and log at programmable intervals for dynamic data acquisition and evaluation. Other sensors, such as a phototransistor or photodiode, may also be used as an optical sensor within sensor housing 16. Other types of light sources, such as laser, incandescent, infrared or ultraviolet light, and other wavelengths may also be used, with corresponding changes in the light sensor as will be understood by those of ordinary skill in the art. Tubing 32, through which fluid passes, is insertable in fluid communication with venturi injector 26 and outlet port 36 and configured to pass through sensor housing 16 in a manner that allows light from a light source to contact the fluid in tubing 32 and be detected by an optical sensor to obtain a reading indicating the level of biofilm growth within tubing 32. Most preferably, these components are configured so that light passed is directed at tubing 32 in a direction substantially perpendicular to the direction of fluid flow through tubing 32. Once a biofilm grows within tubing 32 to a predetermined level, tubing 32 may be removed from monitoring system 10 and replaced with a new piece of tubing 32 to begin the monitoring process over, as more fully described below.

A controller or microcontroller 14 is also preferably disposed within housing 12. Controller 14 is connected to an optional external display/user interface 38, valve 22, the light source and optical sensor within sensor housing 16, and optional USB or data port 29, as shown by dashed lines in FIG. 1. Controller 14 sends and receives signals or data from the connected components of monitoring system 10. Controller 14 sends a signal to valve 22 to open and close the valve to allow dye to be periodically injected into the fluid within tubing 32. Controller 14 also sends signals to a light source within sensor housing 16 to periodically direct light to tubing 32, which is detected or measured by an optical sensor within sensor housing 16. That optical sensor then sends a signal or data back to controller 14, indicating the level, if any, of biofilm growth within tubing 32. The level of biofilm growth within tubing 32 is indicative of biofilm growth on components of the fluid system. Controller 14 sends information regarding the measurements of biofilm growth to an external display/user interface 38. One or more data ports 29 are preferably disposed in housing 12 and connected to controller 14, to allow monitoring system 10 to connect to other devices (such as a computer or server), to an external power source, or to receive removable memory cards. One or more data ports 29 (such as a USB port) allow controller 14 to send or receive data, such as software updates, operational instructions (such as whether to run a low resolution or high resolution test or instructions or data regarding an adjustment to an operating parameter for the fluid system in response to the biofilm measurement), and/or biofilm growth measurements based on signals from the optical sensor. These ports would interact with the controller 14 of monitoring system 10 according to known methods understood by those of ordinary skill in the art.

Controller 14 preferably has sufficient memory to store readings or measurements from the optical sensor for a period of time. A preferred controller 14 has electrically erasable programmable read-only memory (EEprom) of 256 bytes, with each byte storing 8 bits of information (2 digit hexadecimal number). An analog to digital converter on the controller 14 is preferably a 10 bit module, so that that each measurement will have 10 bits of binary information. Controller 14 and optical sensor in sensor housing 16 are preferably configured to allow operation in a low resolution (or standard) mode and a high resolution mode. In low resolution mode, the A/D measurement is bit shifted to save room on the chip for data logging purposes. When run in high resolution mode, the A/D measurement is split into 2 'cells' of the EEprom, using more space, but quadrupling the resolution. Other configurations and storage capabilities may be use with monitoring system 10, as will be understood by those of ordinary skill in the art. Controller 14 may be battery powered, connected to an external power source (such as A/C power), or both. Battery power provides flexibility in placement of monitoring system 10, since it would not need to be placed near an outlet or other power source. Battery power may be provided by a battery pack 50 as shown in FIG. 8. Battery pack 50 preferably comprises around four standard batteries (preferably AA batteries, but AAAA to D batteries may also be used) having a well-known total size range of around 33.2 to 132.8 mm in width/combined diameters for four batteries and around 42.5 to 61.5 mm in length, depending on the size of the battery ranging from AAAA to D. Sensor housing 16 is preferably substantially rectangular in shape, having a length, width, and height as also shown in FIGS. 8-10. At least one of the length, width, or height of sensor housing 16 is preferably around 33.2 to 132.8 mm and at least one other of the length, width, or height of sensor housing 16 is around 42.5 to 61.5 mm as shown in FIG. 8 (compared to size of battery pack 50). Additionally, at least one of the length, width, or height of sensor housing 16 is preferably around the size of a standard USB connection end insertable into USB port 29 as shown in FIG. 9.

Figure 2:
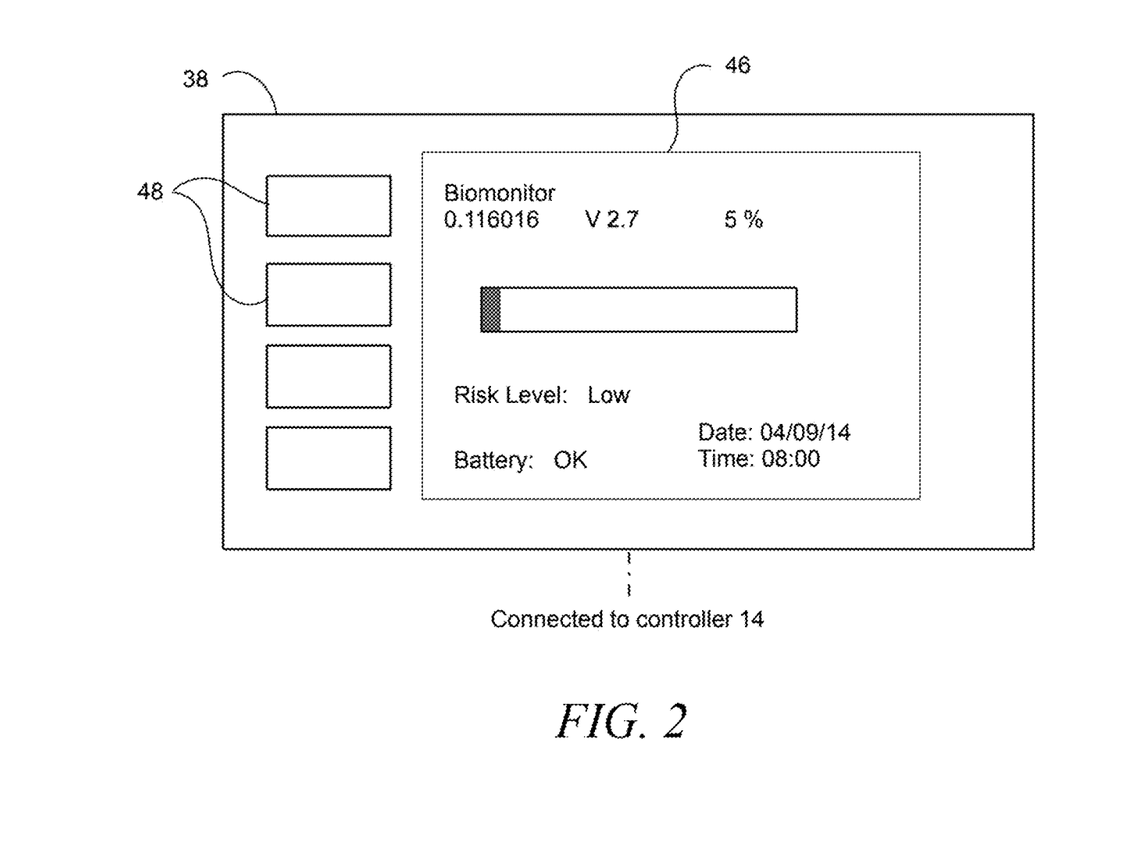
FIG. 2 is a simplified diagram of an external display/user interface for a monitoring system according to the preferred embodiment.

A screen or external display/user interface 38 is preferably located on an outer face of housing 12 in a location that is easily accessible by a user or operator. The external display/user interface 38 preferably comprises a display screen 40 to provide information regarding operation of monitoring system 10 and the level of biofilm growth within tubing 32. For example, as shown in FIG. 2, a visual representation of the biofilm formation displayed on screen 46 may include a bar that increases in size as greater deposits are detected and/or a numerical or percentage indication of growth. Screen 46 may also include an alphanumeric status, indicating a level of risk associated with the degree of biofilm growth detected, which may flash if an alarm status is reached to indicate that attention or action is needed. Monitoring system 10 may also include an audible alarm or series of alarms corresponding to increasing levels of biofilm growth detected. Screen 46 may also indicate the status or strength of the battery for monitoring system 10 (if battery powered), display the date and time, and/or other information related to monitoring system 10, such as a version associated with the equipment or programming for controller 14. External display/user interface 38 also preferably comprises a plurality of buttons or knobs 48 that allow an operator to input information and/or manually operate various components of monitoring system 10. Buttons or knobs 48 may alternatively be touch screen type buttons included within display screen 46. Buttons or knobs 48 (or touch screen) allow a user to provide inputs to monitoring system 10, such as selection of the particular test to be performed (low resolution or high resolution), changing measuring cycle timing, resetting the system for a new monitoring cycle, recall of stored data from prior tests, or sending electronic data or commands to other devices or components of the fluid system being tested or a control system that controls various components of the fluid system. In conjunction with the controller 14, the external display/user interface 38 may be programmed for a variety of functions as will be understood by those of ordinary skill in the art.

When monitoring system 10 is connected to a fluid system, a portion of fluid from the fluid system is diverted to monitoring system through tubing 42 and into tubing 32. Controller 14 is preferably preprogrammed to periodically initiate a measurement cycle, with multiple measurement cycles being completed within each monitoring cycle. Although other measurement cycle times may be used, a once per day cycle is preferred. A measurement cycle begins with controller 14 sending a signal to open valve 22 to allow dye from reservoir 18 to be injected into the fluid through venturi injector 26. The suction from the venturi injector 26 is activated when valve 22 is open, allowing a small quantity of dye to be introduced into the water or other fluid that will flow to sensor housing 16 through tubing 32. In normal operation, valve 22 is open for between ½ a second and 2 seconds once per day and in its non-activated mode is closed, which prevents unintended release of dye and failure of monitoring system 10 if power to the monitoring system 10 is lost. During normal operation of a measurement cycle, controller 14 will turn on a light source (LED) in sensor housing 16 for approximately 60 seconds and check the corresponding voltage at an optical sensor within sensor housing 16. An analog to digital converter takes the analog voltage and converts it to a 10 bit digital hexadecimal value and makes comparisons to an initial state reading. The first reading or measurement during a monitoring cycle is saved as the initial state or comparison value. As biofilm grows on tubing 32, the sensor voltage will increase, which causes a greater deviation from the initial value. With each measurement cycle, the results of the measurement and/or comparison to the initial reading are preferably displayed on display screen 46 and stored in memory.

Controller 14 may also optionally operate a high resolution measurement cycle if biofilm is detected. A high resolution measurement cycle may be preprogrammed to automatically run if biofilm is detected at a predetermined level or may be manually run by selecting or activating a button 48 on external display/user interface 38. If a reading or measurement during a normal operation measurement cycle indicates the presence of biofilm in tubing 32, then controller 14 may confirm the presence of biofilm by running a high resolution test where a reading is made immediately before and after dye has been introduced into tubing 32. Under normal operating conditions, the dye will not impact the voltage change on the optical sensor; but by running a high resolution reading it will be possible to detect small changes associated with the dye changing the color of the biofilm. This high resolution test may be used as a confirmation step to identify the fouling as biofilm and not just mineral deposits. The results of the high resolution test may be displayed as are the results of a normal operation test on screen 46 or may be separately displayed to distinguish between normal operation (low resolution) results and high resolution results. One or more high resolution tests may be run in each monitoring cycle.

If any measured or calculated result, comparison of results, difference in results, or deviation is out of a predetermined or pre-set range of desired values or is above or below a pre-determined or pre-set threshold value, then monitoring system 10 may generate an alarm indicating that an adjustment or modification of one or more operating parameters for the fluid system is needed. An alarm may be visual, audible, or both, and may be communicated locally at housing 12 or remotely at another location, such as a control room for the fluid system or via email or text to an operator. Preferably, a warning message, such as an increase in risk level from "low" to "moderate" and ultimately to "high" (although other wording and additional intermediate levels may also be used), is displayed on screen 46. As the amount of fouling increases during a monitoring cycle, the severity of the warning level also preferably increases. Audible alarms may also be used in place of or in conjunction with visual indicators on screen 46. Most preferably, an initial alarm within a monitoring cycle is triggered when the difference between the sensor reading and the initial reading reaches around 15% difference. Additional, higher level alarms, are preferably triggered when that difference is around 30%, 50%, and 65%.

When an alarm is triggered, it indicates that there is biofilm growth within tubing 32 or that the amount of biofilm growth has reached or exceeded a predetermined level, which indicates the presence of biofilm growth (and a similar amount of biofilm growth) on other components of the fluid system. To keep the fluid system operating properly, it is important to treat the fluid system to remove the biofilm and help control re-growth. An alarm triggered by monitoring system 10 indicates that action is needed to adjust one or more operating parameters of the fluid system to treat the biofilm growth. Such adjustments are preferably automatically made when biofilm growth is detected or when a certain level of biofilm growth is detected, in response to an alarm signal from controller 14. Most preferably, controller 14 is configured to automatically initiate such adjustments by sending signals to the separate control system for the fluid system or by directly sending signals to smart components within the fluid system, such as opening or closing valves to release a dose (or a series of doses) of biocide or other treatment products into the fluid system. Such adjustments may also be performed manually, manually entered into the monitoring system 10 to be communicated to a separate control system for the fluid system to automatically carry out the adjustment commands, or may be manually entered into a separate control system for the fluid system and then automatically carried out by that control system. Other adjustments in operating parameters may include altering the amount of non-biocide treatment products added to the fluid system, adjusting blowdown rate, adjusting fresh-water make-up rate, increasing or decreasing flow rates through the fluid system, or other adjustments as needed to remove biofilm and help control regrowth. Controller 14 also preferably sends an email or text message to designated personnel or computer stations when an alarm is triggered and when any operational adjustments or treatment dosing has automatically occurred.

Monitoring system 10 can also be used to determine the effectiveness of the adjustments made in treating the biofilm. By continuing to monitor the level of biofilm within tubing 32, monitoring system 10 can determine whether the operating adjustments are sufficient to remove the biofilm from components in the fluid system. Once the level of biofilm in tubing 32 returns to zero or near zero, a monitoring cycle is completed and a new monitoring cycle begins again. Alternatively, housing 12 and sensor housing 16 may be opened, tubing 32 disconnected and removed and a new piece of tubing 32 inserted to begin a new monitoring cycle. For example, as shown in FIG. 10, a top 52 of sensor housing 16 is openable to allow the narrow lumen tubing 32 to be inserted into a housing slot 54 (the portion of the tube in the slot is the measurement area where biofilms grows and is measured inside sensor housing 16). Monitoring system 10 may also be manually reset to initiate a new monitoring cycle. Monitoring cycles are preferably repeated to continuously monitor biofilm growth within the fluid system.

Figure 3:
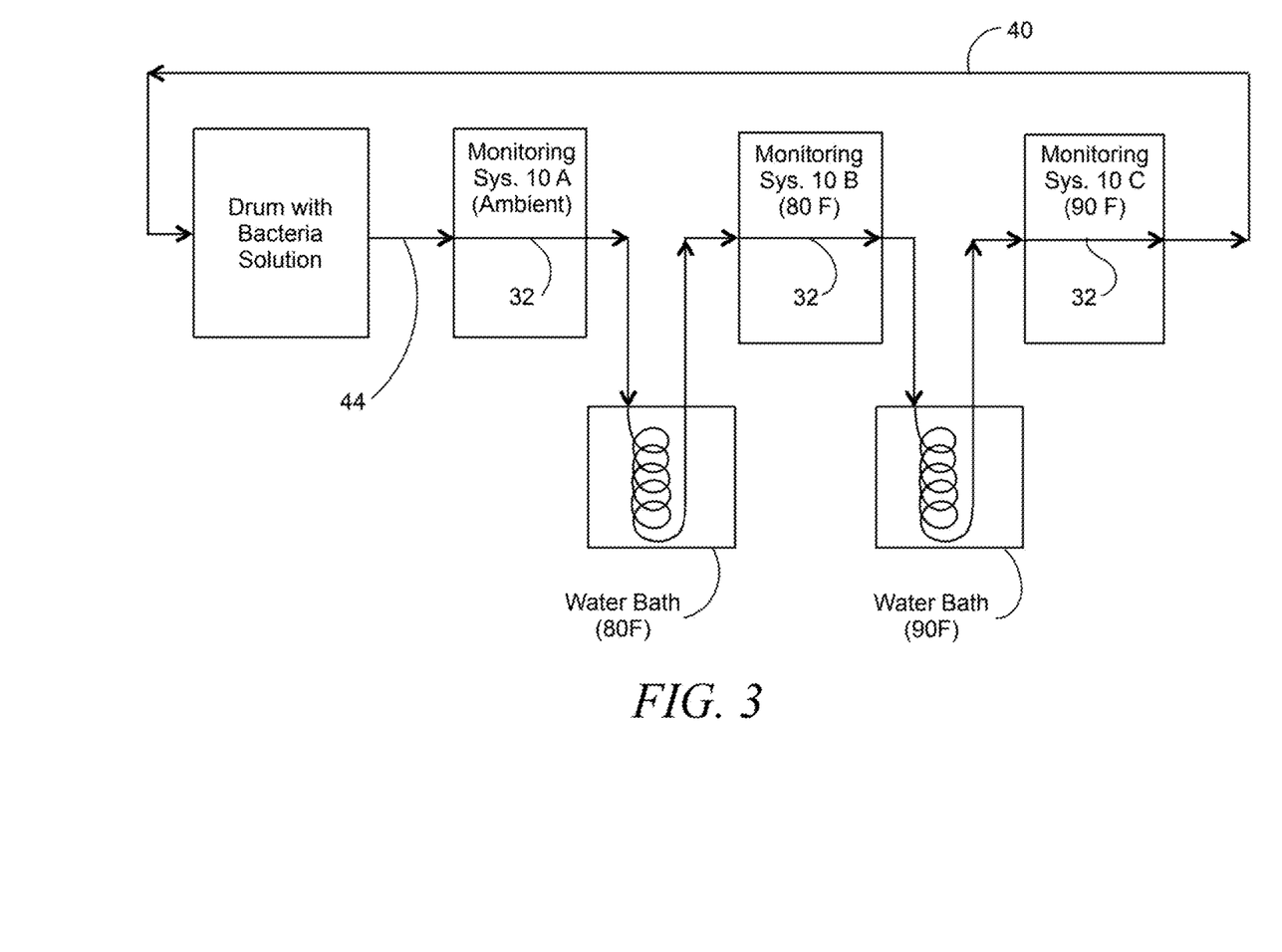
FIG. 3 is a block diagram showing a temperature controlled test configuration for several monitoring systems according to an embodiment of the invention.

An embodiment of the monitoring system 10 and method of monitoring biofilm growth was tested at various temperature ranges to confirm the effectiveness of the monitoring system 10, as well as to determine the impact of temperature on propagation of biofilm and to correlate output signals of the optical sensor to a biofilm growth rate. Three identical monitoring systems (shown as 10A, 10B, and 10C in FIG. 3) were connected in series to a 30 gal drum of tap water (to simulate the fluid system), as shown in FIG. 3. The drum of tap water was inoculated with overnight cultures of Pseudomonas species (5 mL) and Bacillus species (5 mL) in TSB (tryptic soy broth). Each monitoring system comprises a controller and a sensor housing have a light source and optical sensor, as shown in FIG. 1. The 30 gal drum containing the bacterial latent water was maintained at ambient temperature of about 72° F. and it was used to deliver a constant flow through the entire PVC tubing (e.g. tubing 44, 32, and 40) for all three monitoring systems 10A, 10B, and 10C. Temperature controlled water baths set at 80° F. and 90° F. were placed between the first and second monitoring systems (between 10A and 10B) and between the second and third monitoring systems (between 10B and 10C), respectively. The water baths were used to raise the temperature of water flowing through the second and third monitoring systems 10B and 10C to simulate the temperature environments that may be encountered in a cooling tower system in the field (as an example of a type of fluid system with which a monitoring system according to the invention could be used). Coiled sections of the PVC tubing were submerged in the temperature controlled water baths to give the internal solution flowing within the tubing enough residence time to equilibrate to the bath temperature while within the respective coiled zones, so the water fed into monitoring system 10B was around 80° F. and the water fed into monitoring system 10C was around 90° F.

Noting the time and date for the start of the experiment, some of the bacteria latent solution was pumped into the monitoring systems to fill the tubing and the water was then allowed to sit stagnant for almost 16 hours to initiate the biofilm growth in the tubing 32 within each monitoring system. The water was then continuously pumped through each monitoring system 10A, 10B, and 10C and recycled back to the drum for a monitoring cycle duration of 16 days. The controller 14 in each monitoring system in this experiment operated 24 measuring cycles per day over 16 days (although other time periods for the monitoring cycle and each measuring cycle could also be used), collecting a low resolution measurement from the optical sensor for each measuring cycle. High resolution tests were not run for this experiment. Erythrosine was used as the dye and injected into the drum, rather than using a dye reservoir and venturi injector for each monitoring system 10A, 10B, and 10C. For comparison to the optical sensor readings and for calibration of those readings, bioassay and microscopic analysis of sections of the narrow lumen tubing 32 from each monitoring system were analyzed. A 2 cm sample section was cut from the narrow lumen tubing 32 in each monitoring system (10A at ambient temperature, 10B at 80° F., and 10C at 90° F.) and a thin section of each tube section was isolated for brightfield microscopic analysis. The tubing used for the experiment was long enough to allow sections to be removed for testing and the tubing resected over the course of the experiment.

Figure 4:
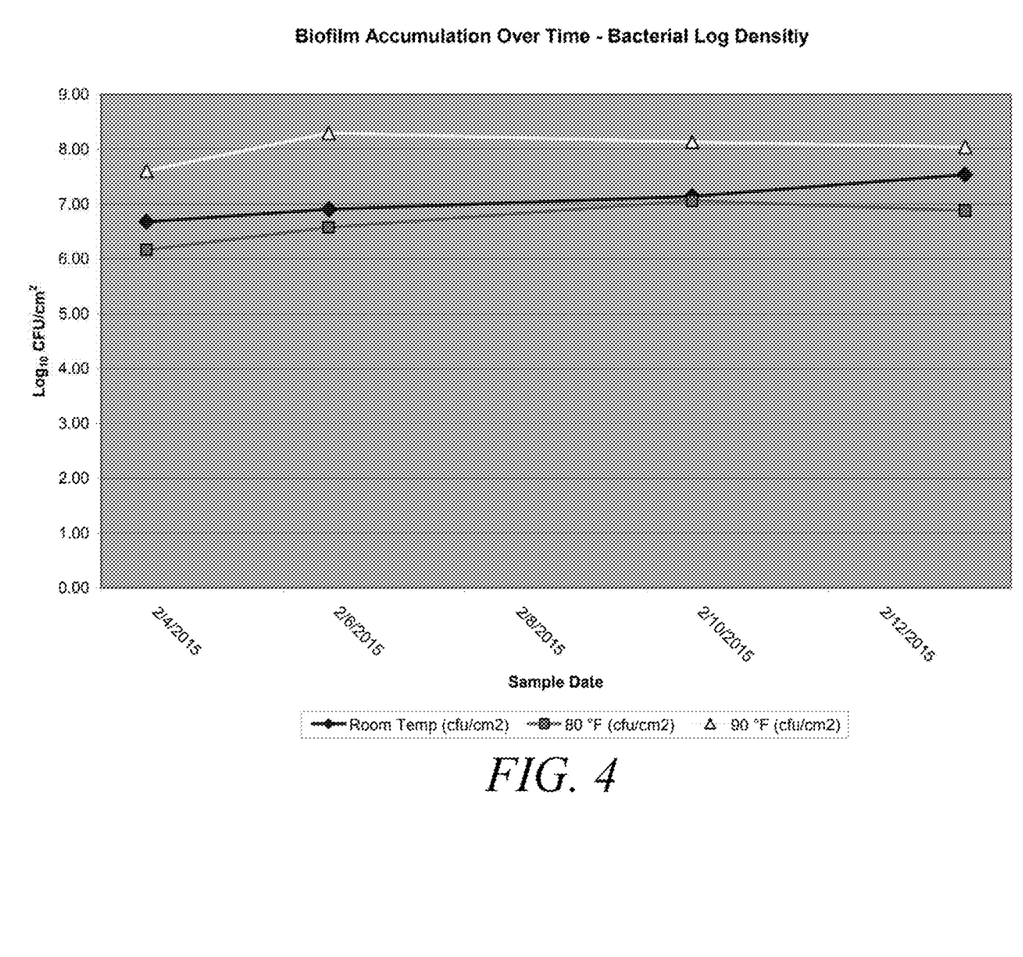
FIG. 4 is a graph showing the results of a viability assay to determine biofilm density in sections of narrow lumen tubing in an experiment using three monitoring systems according to a preferred embodiment.

Additionally, a viability assay was performed on each section of tubing to determine the biofilm density ($Log_{10}$ CFU per $cm^2$) on several days between days 7 and 16 of the monitoring cycle. The results of this viability assay are shown in FIG. 4. The tubing from monitoring system 10C at 90° F. showed a markedly higher initial biofilm growth, while the tubing from monitoring system 10A at ambient temperature and 10B at 80° F. were tracking similarly and approached the same cell density by Day 16 to within one log. The time and date of each section removal was noted for comparison to the data obtained from the optical sensor and stored on the microcontroller. It was found that the signals from the optical sensor correlated to the increase in biofilm growth to allow calibration of the optical sensor signals to biofilm density.

Another experiment was conducted using three monitoring systems 10A, 10B, and 10C. Each monitoring system was identical and comprises a controller, inlet and outlet ports, narrow lumen tubing, and a sensor housing have a light source and optical sensor, similar to that shown in FIG. 1 This experiment did not include any temperature modification and the monitoring systems were not connected in series as in the previously described experiment. A biofilm growth promoting solution containing cultures of Pseudomonas species (5 mL) and Bacillus species (5 mL) in TSB (tryptic soy broth) was added to the tubing (e.g. tubing 32) in each monitoring system and allowed to sit for 8 hours to initiate biofilm growth. A biofilm revealing dye (erythrosine) was added to the biofilm forming solution at a rate of 3 drops per liter of solution. For purposes of this experiment, the dye was not injected into flowing water through a venturi as previously described with respect to FIG. 1. After biofilm initiation, tap water at ambient temperature (around 72° F.) was filtered with a granulated activated carbon filter and then continuously pumped through the tubing of each monitoring system for a monitoring cycle of 14 days. The controller 14 in each monitoring system operated 14 measuring cycles, one for each day of the monitoring cycle (although other time periods for the monitoring cycle and each measuring cycle could also be used), collecting a low resolution measurement from the optical sensor for each measuring cycle. No high resolution tests were run in this experiment. For comparison to the optical sensor readings and for calibration of those readings, bioassay and microscopic analysis of sections of the narrow lumen tubing 32 from each monitoring system were analyzed. Five-seven sample sections of 2 cm-3 cm each were cut from the narrow lumen tubing 32 in each monitoring system and a thin section of each tube section was isolated for confocal microscopic analysis and stereoscopic analysis. The tubing used for the experiment was long enough to allow sections to be removed for testing and the tubing resected over the course of the experiment. Using confocal microscopy and special biofilm fluorescent stains, the thickness of the biofilm layer on the PVC tubing segments was measured and recorded. Additionally, a viability assay was performed on each section of tubing to determine the biofilm density ($Log_{10}$ CFU per $cm^2$). The time and date of each section removal was noted for comparison to the data obtained from the optical sensor and stored on the microcontroller.

Figure 5:
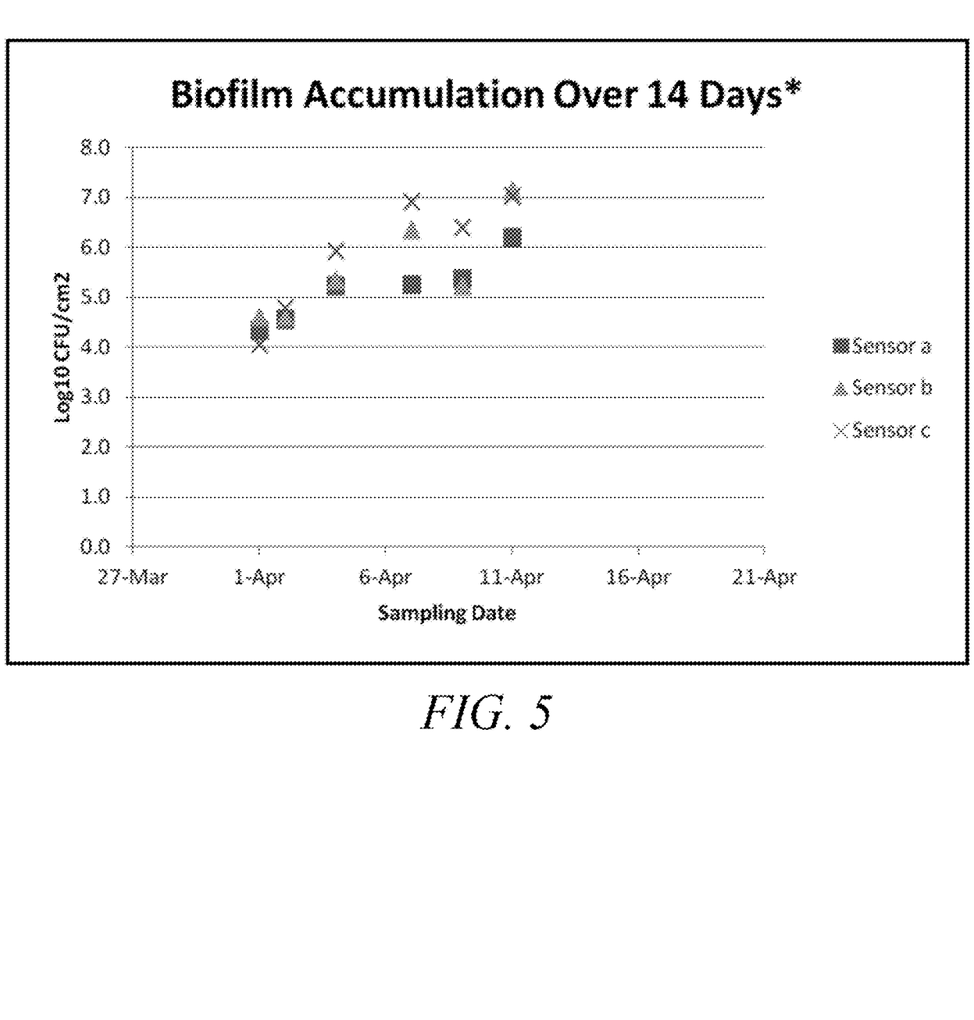
FIG. 5 is a graph showing the results of a viability assay to determine biofilm density in sections of narrow lumen tubing in a second experiment using three monitoring systems according to a preferred embodiment.
Figure 6:
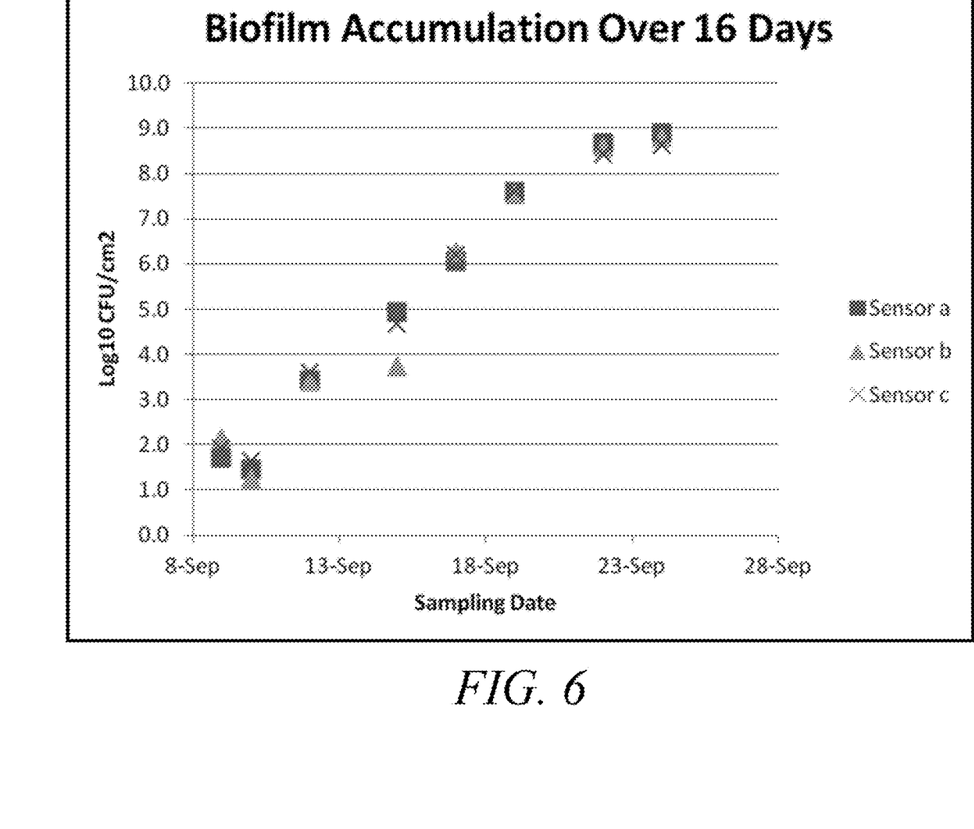
FIG. 6 is a graph showing the results of a viability assay to determine biofilm density in sections of narrow lumen tubing in a third experiment using three monitoring systems according to a preferred embodiment.
Figure 7:
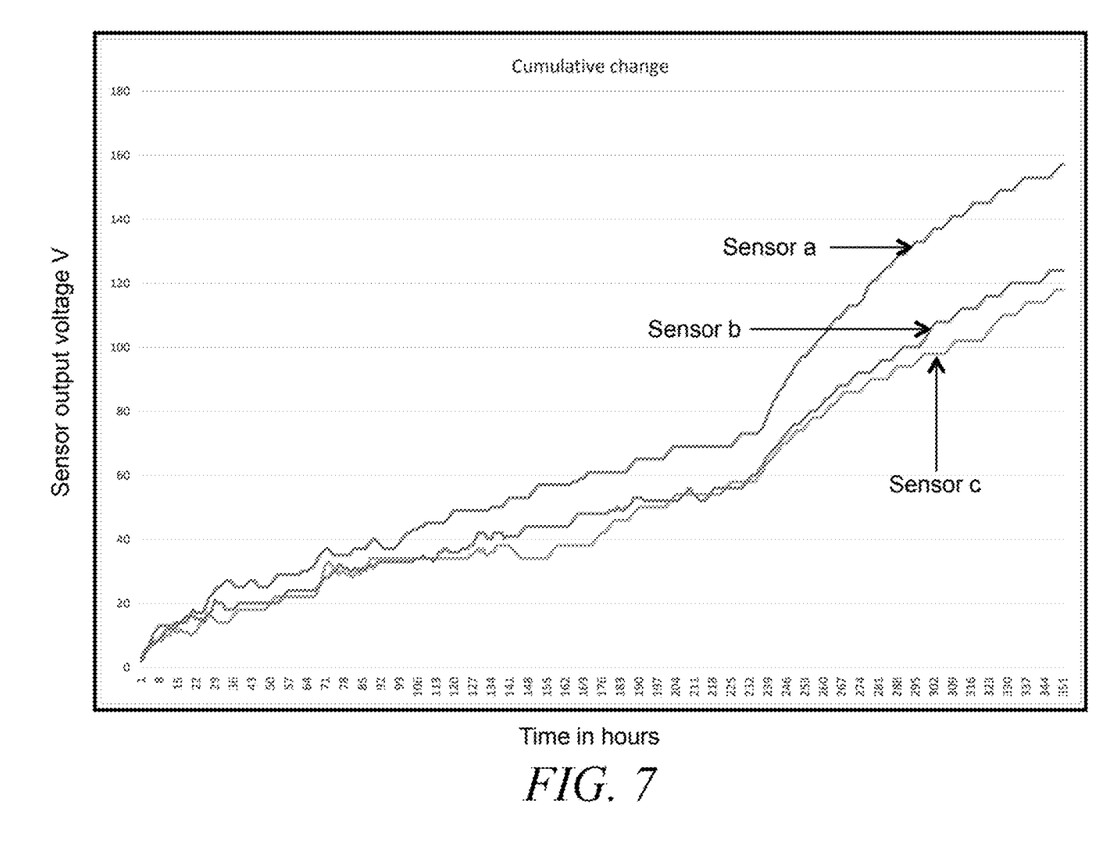
FIG. 7 is a graph showing the output from optical sensors in the three monitoring systems used in the third experiment showing increase in signal corresponding to increase in biofilm thickness.

The results of tubing analysis from this 14 day experiment are shown in FIG. 5. Another experiment was run with this same set-up and methodology for a 16 day monitoring cycle. The results of the tubing analysis from this 16 day experiment are shown in FIG. 6. FIG. 7 shows the shows the output from the optical sensors (voltage) from monitoring systems 10A, 10B, and 10C for the 16 day experiment described above. It can be seen that as the thickness of the biofilm in the tube increases the output signal from the sensor increases, which corresponds to the increase in bacterial counts and to the thickness data observed by the confocal microscopy.

These experiments show that monitoring systems according to preferred embodiments of the invention are capable of bacterial colonization and supporting biofilm growth regardless of temperature of the influent, while also allowing the monitoring systems' optical sensors and controllers to accurately read and track biofilm density over time. Additionally, the use of removable tubing 32 through the monitoring system allows for a measurable method for bioassay and determination of actual cell density, by removal and testing, if so desired.

References herein to calculating or measuring a value or property and the like are intended to include any form of direct measurement, converting data or a signal, making a calculation based on one or more data points or signals, or otherwise comparing, interpreting, correlating, or manipulating one or more data points or signals. Those of ordinary skill in the art will also appreciate upon reading this specification and the description of preferred embodiments herein that modifications and alterations to the system may be made within the scope of the invention and it is intended that the scope of the invention disclosed herein be limited only by the broadest interpretation of the appended claims to which the inventors are legally entitled.

We claim:

1. A detection system for detecting microbiological growth in a flowing fluid system, the detection system comprising:
    a tube comprising an inlet, an outlet, and a measurement area disposed between the inlet and the outlet, the inlet configured to receive a portion of fluid from the flowing fluid system;
    a light source for directing light having a wavelength within a visible spectrum through the measurement area of the tube;
    an optical sensor configured to detect a transmission of the light through the measurement area of the tube and to produce a signal corresponding to the transmission;
    a sensor housing in which the light source, the optical sensor and the measurement area of the tube are disposed; and
    a controller configured to receive the signal from the optical sensor and calculate an amount of the microbiological growth within the tube based on the signal; and
    wherein the tube is configured for laminar flow of the fluid through the measurement area of the tube.

2. The detection system of claim 1 wherein the sensor housing is openable and comprises a slot configured to receive the measurement area of the tube.

3. The detection system of claim 2 wherein the signal is one of a plurality of signals, wherein the controller is further configured to periodically activate the light source and wherein the optical sensor is configured to produce one of the plurality of signals each time the light source is activated.

4. The detection system of claim 3 wherein the controller is further configured to automatically convert each of the plurality of signals into a measurement of the amount of the microbiological growth within the measurement area.

5. The detection system of claim 4 wherein the measurement from one of the plurality of signals is a first measurement;
    wherein the measurement from another of the plurality of signals is a second measurement; and
    wherein the controller is further configured to compare the first measurement to the second measurement or to a first predetermined threshold.

6. The detection system of claim 5 wherein the controller is further configured to adjust an operating parameter of the flowing fluid system when (1) the first measurement reaches, exceeds, or is below the first predetermined threshold or (2) when a comparison of the first measurement and the second measurement reaches, exceeds, or is below a second predetermined threshold or (3) a combination thereof.

7. The detection system of claim 6 wherein the operating parameter is increasing or decreasing (1) a dosage of biocide added to the flowing fluid system, (2) blowdown rate in the flowing fluid system, (3) make-up water rate in the flowing fluid system, (4) flow rates through the flowing fluid system, or (5) a combination thereof.

8. The detection system of claim 2 wherein the tube has an internal diameter of 1 mm to 20 mm;
    wherein the light source comprises an LED; and
    wherein the optical sensor comprises a photodiode or a phototransistor.

9. The detection system of claim 8 wherein the sensor housing is substantially rectangular.

10. The detection system of claim 9 wherein the sensor housing is sized with a width and height each around 2 to 3 times an external diameter of the measurement area of the tube.

11. The detection system of claim 9 wherein the sensor housing has a length, width, and height, at least one of which is sized around 33.2-132.8 mm and at least one other of which is sized around 42.5-61.5 mm.

12. The detection system of claim 8 further comprising a user display that indicates a risk level based on the signal as being between low and high.

13. The detection system of claim 1 wherein the sensor housing is openable and wherein the flowing fluid system is a cooling system or a boiler system comprising a coupon rack and wherein the detection system is disposed near the coupon rack.

14. The detection system of claim 13 further comprising a user display that indicates a risk level based on the signal as being between low and high.

15. A detection system for detecting potential microbiological growth in a flowing fluid system, the detection system comprising:
   a connected tubing segment configured to receive a portion of fluid from the flowing fluid system and selected from a plurality of interchangeable tubing segments each comprising an inlet, an outlet, and a measurement area disposed between the inlet and outlet;
   an outer housing;
   a sensor housing disposed inside the outer housing and configured to receive the measurement area of the connected tubing segment;
   a light source disposed inside the sensor housing for directing light through the measurement area of the connected tubing segment;
   an optical sensor disposed inside the sensor housing and configured to detect transmission of light through the measurement area of the connected tubing segment and to produce a signal corresponding to the transmission; and
   a controller disposed inside the outer housing and configured to receive the signal from the optical sensor and calculate an indicated amount of microbiological growth within the connected tubing segment;
   wherein detection system is an early warning detection system configured for laminar flow of the fluid through the measurement area of the connected tubing segment; and
   wherein the connected tubing segment is configured to be disconnected after an amount of microbiological growth in its measurement area reaches a predetermined level and to be replaced with a new selected one of the plurality of interchangeable tubing segments as the connected tubing segment.

16. The detection system of claim 15 wherein the sensor housing is configured to change between an open position to allow removal and replacement of the connected tubing segment and closed position around the measurement area of the connected tubing segment in use.

17. The detection system of claim 16 wherein the sensor housing is made of solid dark colored material to substantially block external light from entering the sensor housing during use.

18. The detection system of claim 16 further comprising a user display that indicates a risk level based on the signal as being between low and high.

19. The detection system of claim 1 wherein the wavelength is in a range of 545 to 570 nm.

* * * * *